(12) United States Patent
Pittman et al.

(10) Patent No.: US 6,538,169 B1
(45) Date of Patent: Mar. 25, 2003

(54) FCC PROCESS WITH IMPROVED YIELD OF LIGHT OLEFINS

(75) Inventors: Rusty M. Pittman, Chicago, IL (US); Lawrence L. Upson, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/711,576

(22) Filed: Nov. 13, 2000

(51) Int. Cl.[7] .......................... C07C 4/06; C10G 11/05; C10G 11/18

(52) U.S. Cl. ...................... 585/653; 585/651; 585/648; 585/644; 585/650; 208/118; 208/114; 208/120.1

(58) Field of Search .................................. 585/648, 644, 585/650, 651, 653; 208/118, 114, 120.1

(56) References Cited

U.S. PATENT DOCUMENTS

| | | | |
|---|---|---|---|
| 3,888,762 A | 6/1975 | Gerhold | 208/120 |
| 4,717,466 A | 1/1988 | Herbst et al. | 208/113 |
| 4,787,967 A | 11/1988 | Herbst et al. | 208/74 |
| 4,853,105 A | 8/1989 | Herbst et al. | 208/74 |
| 4,871,446 A | 10/1989 | Herbst et al. | 208/152 |
| 4,980,053 A | 12/1990 | Li et al. | 208/120 |
| 4,990,314 A | 2/1991 | Herbst et al. | 422/144 |
| 5,296,131 A | 3/1994 | Raterman | 208/113 |
| 5,372,704 A | 12/1994 | Harandi et al. | 208/74 |
| 5,389,232 A | 2/1995 | Adewuyi et al. | 208/120 |
| 5,597,537 A | 1/1997 | Wegerer et al. | 422/144 |
| 5,858,207 A | 1/1999 | Lomas | 208/113 |
| 5,965,012 A | 10/1999 | Lomas | 208/113 |
| 5,997,728 A | 12/1999 | Adewuyi et al. | 208/120.01 |
| 6,010,618 A | 1/2000 | Lomas | 208/113 |
| 6,106,697 A | 8/2000 | Swan et al. | 208/77 |

FOREIGN PATENT DOCUMENTS

| | | |
|---|---|---|
| WO | WO 95/27019 | 10/1995 |
| WO | WO 00/31215 | 6/2000 |
| WO | WO 00/40672 | 7/2000 |

OTHER PUBLICATIONS

David Hutchinson and Roger Hood, *Catalytic Cracking to Maximize Light Olefins*, Petrole Et Techniques, Mar.–Apr. 1996, at 29.

Charles Hemler and Lawrence Upson, *Maximize Propylene Production*, presented at the European Refining Technology Conference, Berlin, Germany, Nov. 16–18, 1998.

*Primary Examiner*—Thuan D. Dang
(74) *Attorney, Agent, or Firm*—John G. Tolomei; James C. Paschall

(57) ABSTRACT

An FCC process for obtaining light olefins comprises contacting a hydrocarbon feed stream with blended catalyst comprising regenerated catalyst and coked catalyst. The catalyst has a composition including a first component and a second component. The second component comprises a zeolite with no greater than medium pore size wherein the zeolite comprises at least 1 wt-% of the catalyst composition. The contacting occurs in a riser to crack hydrocarbons in the feed stream and obtain a cracked stream containing hydrocarbon products including light olefins and coked catalyst. The cracked stream is passed out of an end of the riser such that the hydrocarbon feed stream is in contact with the blended catalyst in the riser for less than or equal to 2 seconds on average.

17 Claims, 2 Drawing Sheets

FCC PROCESS WITH IMPROVED YIELD OF LIGHT OLEFINS

BACKGROUND OF THE INVENTION

1. Field of the Invention

This invention relates to the fluidized catalytic cracking (FCC) conversion of heavy hydrocarbons into light hydrocarbons with a fluidized stream of catalyst particles. More specifically, this invention relates to an FCC process for the production of light olefins.

2. Description of the Prior Art

Catalytic cracking is accomplished by contacting hydrocarbons in a reaction zone with a catalyst composed of finely divided particulate material. The reaction in catalytic cracking, as opposed to hydrocracking, is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons in a fluidized stream of catalyst, transporting catalyst between reaction and regeneration zones, and combusting coke in the regenerator are well known by those skilled in the art of FCC processes.

Propylene is conventionally produced through FCC processes, dehydrogenation processes, and predominantly from steam cracking processes. The demand for propylene is projected to begin to outstrip supply. FCC units are filling some of this growing demand for propylene. Typically, however, FCC units produce only around 5 wt-% of propylene. Consequently, modifications to FCC units that can increase propylene production are necessary. Several references disclose modified FCC processes to improve propylene yields.

Many of these processes increase propylene yields by increasing conversion by utilizing longer reaction times and hot catalyst temperatures. One such process called deep catalytic cracking ("DCC") requires 5–10 seconds of contact time to increase propylene yields. However, this process also yields a relatively substantial quantity of undesirable dry gas; i.e., hydrogen, ethane and methane. See David Hutchinson and Roger Hood, *Catalytic Cracking to Maximize Light Olefins*, PETROLE ET TECHNIQUES, March–April 1996, at 29. U.S. Pat. No. 4,980,053 also discloses a deep catalytic cracking process that cracks over a mixture of Y-type zeolite and a pentasil, shape-selective zeolite to give substantial yields of propylene. Similarly, this patent discloses an effort to prolong the catalyst contact time which is probably the reason for it reporting relatively high yields of dry gas.

Other patents disclosing short catalyst contact times do not recognize significant light olefin yields. U.S. Pat. No. 5,965,012 discloses an FCC process with a catalyst recycle arrangement with a very short contact time of the feed and catalyst. However, the short contact time does not take place in the riser. Cracking takes place in a chamber where regenerated and carbonized catalyst contacts the feed. The cracked products are immediately withdrawn from the cracking chamber and separated from the catalyst in a conduit which is separate from the riser. U.S. Pat. No. 6,010,618 discloses another FCC process which provides for very short catalyst-to-feed contact time in the riser by quickly removing cracked product from the riser well below halfway to the outlet of the riser. U.S. Pat. No. 5,296,131 discloses ultra-short FCC catalyst contact times to improve selectively to gasoline while decreasing coke and dry gas production. These patents do not target significant production of light olefins.

U.S. Pat. No. 5,389,232 discloses quenching the feed and catalyst mixture with naptha in the riser to shorten the catalyst-to-feed contact time to obtain light olefins. This patent, however, reports relatively low yields of light olefins.

Other patents disclose processes that use catalyst recycle without regeneration. U.S. Pat. No. 3,888,762 discloses sending stripped catalyst and regenerated catalyst to the base of the riser without mixing. U.S. Pat. No. 4,853,105 discloses an FCC process whereby stripped, coked catalyst is recycled to the riser just less than mid-way up the riser. This stripped, coked catalyst contacts feed in the riser for less than 1 second but the feed also has contact time with regenerated catalyst from about 10 to about 50 seconds. U.S. Pat. No. 5,858,207 discloses an FCC process wherein regenerated catalyst and stripped coked catalyst are subjected to secondary stripping before being returned to the riser to contact feed. U.S. Pat. No. 5,372,704 discloses an FCC process wherein spent catalyst from a first FCC unit is charged to a riser of a second naphtha cracking unit and then recycled back to the riser of the first FCC unit.

U.S. Pat. Nos. 4,990,314, 4,871,446, and 4,787,967 disclose two component catalyst FCC systems in which a portion of the catalyst is recycled back to the riser without regeneration. Specifically, one component of the catalyst typically includes a large-pore zeolite for cracking the larger molecular hydrocarbons and the second component includes a medium pore zeolite for cracking the smaller molecular hydrocarbons. These patents, by recognizing that the catalyst component with medium pore zeolite are susceptible to hydrothermal degradation, attempt to recycle a homogeneous composition of the catalyst component with medium pore zeolite back to the riser without undergoing regeneration. The exclusion of the catalyst component with medium pore zeolite from the regeneration zone requires either special configuration of the catalyst matrix and/or complex design of the apparatus. U.S. Pat. No. 4,717,466 discloses a variant of this process wherein two risers are utilized. One riser has a greater concentration of ZSM-5 catalyst component in a base with a larger diameter for prolonged contact time with a lighter feed.

PCT Publication WO 95/27019 reports aggregate yields of 26.2 wt-% of ethylene, propylene and butylene in a circulating fluidized bed reactor having a relatively short residence time of 0.1 to 3.0 seconds. The reaction zone disclosed in this application terminates at an external cyclone which separates catalyst and products. The catalyst is stripped and sent either to the base of the reaction zone or a circulating fluidized bed regenerator. This publication does not teach use of a medium or smaller pore zeolite in the catalyst composition.

Some do not use a medium to smaller pore zeolite in the catalyst composition, perhaps, for fear that the concentration of the larger pore or amorphous catalyst would be insufficient to crack the feed down to naptha range molecules. Two cracking steps have to take place to obtain light olefins. First, a catalyst component containing a large pore zeolite and/or an active amorphous material cracks the feed into naphtha range hydrocarbons. Second, a catalyst component containing a medium or small pore zeolite cracks the naphtha range hydrocarbons into light olefins. The medium or small pore zeolite cannot crack the large hydrocarbon molecules in the feed. Hence, the concern that a high concentration of the medium or small pore zeolite component in the catalyst composition could unduly dilute the amorphous or large pore catalytic component to restrain the first step of cracking FCC feed down to naphtha range hydrocarbons.

U.S. Pat. No. 6,106,697 avoids this concern by using a two-stage catalytic cracking system wherein a large pore zeolite component cracks the feed in an FCC unit down to naphtha range hydrocarbons which is then cracked over a medium to small pore zeolitic catalyst component in a second FCC unit to get light olefins. U.S. Pat. No. 5,997,728 discloses an FCC process that cracks feed over a catalyst composition containing relatively large proportions of medium or smaller pore zeolite catalyst and large pore zeolite for 5 seconds of catalyst contact time to obtain good yields of propylene but with high yields of dry gas. However, PCT Publication WO 00/31215 discloses a catalytic cracking process which uses a ZSM-5 and/or ZSM-11 zeolite component on a substantially inert matrix material in a catalytic cracking process to obtain high yields of light olefins U.S. Pat. No. 5,597,537 teaches an FCC process that uses a high ratio of catalyst to feed and higher regenerator temperatures to ensure that gasoline fraction olefins will overcrack to provide a high yield of $C_3$ and $C_4$ olefins. This patent also teaches recycling part of the coked catalyst to a mixing chamber at the base of the riser while transporting another portion of the coked catalyst to the regenerator for regeneration. The regenerated catalyst portion and the recycled, coked catalyst portion are combined in a blending vessel and allowed to thermally equilibrate before being introduced to the riser to catalyze fresh feed. Although this patent does indicate that the disclosed process could be used for lower residence time cracking, it explains that lower residence times are desired to prevent catalyst from coking, not to yield higher quantities of $C_3$ and $C_4$ olefins. This patent also teaches adding a medium pore zeolite component to the catalyst composition in an effort to prevent catalyst coking. However, it does not couple the use of a medium pore zeolite component and short contact times to obtain greater yields of light olefins. This patent reflects the concern that a large pore zeolite and/or active amorphous containing catalyst component that is diluted with a medium pore zeolite component and coked from recycling without regeneration may not be sufficiently active to crack feed down to naptha range hydrocarbon. Hence, the desire to minimize coking.

It is an object of this invention to provide a FCC process that produces high yields of light olefins with less production of dry gas.

SUMMARY OF THE INVENTION

An FCC process is modified to produce greater yields of light olefins; particularly, ethylene, propylene and butylene with less production of dry gas; i.e., hydrogen, methane and ethane at relatively high conversion.

We have discovered that recycling coked catalyst including a large pore zeolite and/or an active amorphous material and a zeolite with no greater than medium average pore size and blending it with regenerated catalyst improves the yield of light olefins and the overall conversion. We have discovered this to be the case even at lower riser residence times.

Additionally, the lower temperature of the catalyst resulting from blending hot regenerated catalyst and cooler recycled catalyst improve olefin selectivity.

Specifically, an embodiment of the present invention is a process for fluidized catalytic cracking of a hydrocarbon feed stream to obtain light olefins. The process comprises contacting the hydrocarbon feed stream with a blended catalyst comprising regenerated catalyst and coked catalyst. The catalyst has a composition including a first component comprising a large pore molecular sieve and/or an active amorphous material and a second component comprising a zeolite with no greater than medium pore size. The zeolite with no greater than medium pore size comprises at least 1.0 wt-% of the catalyst composition. The contacting of the catalyst in the feed stream occurs in a riser to crack hydrocarbons in the feed stream and obtain a cracked stream containing hydrocarbon products including light olefin and coked catalyst. The cracked stream is passed out of an end of the riser so that the hydrocarbon feed stream is in contact with the blended catalyst in the riser for less than or equal to 2 seconds on average. The hydrocarbon products including light olefins are separated from the coked catalyst. A first portion of the coked catalyst is passed to a regeneration zone wherein coke is combusted from the catalyst to produce regenerated catalyst. The regenerated catalyst has substantially the same relative proportions of the first component and the second component as the blended catalyst that contacts the hydrocarbon feed stream. The second portion of the coked catalyst is blended with the regenerated catalyst to make the blended catalyst. Then the blended catalyst is introduced to the riser.

In another embodiment, the catalyst composition may comprise up to 80 wt-% of the catalyst composition. In a further embodiment, the molecular sieve may be either an X-type or a Y-type zeolite.

In another embodiment, the second portion of the coked catalyst and the regenerated catalyst are blended outside of the riser before contacting the feed stream.

Other embodiments of the present invention include the partial pressure of the hydrocarbons in the riser being less than or equal to 172 kPa (25 psia); a diluent in the riser being greater than or equal to 10 wt-% of the feed stream; a ratio of catalyst to feed in the riser being greater than or equal to 10; a ratio of coked catalyst to regenerated catalyst in the riser being in the range of 0.3 to 3.0; a temperature of the cracked stream at the top end of the riser being in the range of 510° to 621° C. (950° to 1150° F.); a temperature of the blended catalyst being greater than or equal to 28° C. (50° F.) lower than the temperature of the regenerated catalyst coming from the regenerator; and the zeolite with no greater than medium pore size comprising at least 1.75 wt-% of the blended catalyst composition.

In another embodiment, the present invention comprises a process for fluidized catalytic cracking of a hydrocarbon feed stream to obtain light olefins. The process comprises contacting the hydrocarbon feed stream with a blended catalyst at an initial temperature of 621° to 677° C. (1150° to 1250° F.) in a reactor conduit to crack hydrocarbons in the feed stream and to obtain a cracked stream containing hydrocarbon products including light olefins and coked catalyst. The blended catalyst comprises regenerated catalyst and coked catalyst. The catalyst has a catalyst composition including a first component and a second component comprising a molecular sieve with no greater than medium average pore size. The cracked stream is passed out of the reactor conduit at a temperature of 538° to 593° C. (1000° to 1100° F.) such that the hydrocarbon feed stream is in contact with the blended catalyst in the riser for less than or equal to 2 seconds on average. The hydrocarbon products including light olefins are separated from the coked catalyst. The first portion of the coked catalyst is passed to a regeneration zone and coke is combusted from the catalyst to produce regenerated catalyst. The regenerated catalyst has substantially the same relative proportions of the first catalyst component and the second catalyst component as the blended catalyst that contacts the hydrocarbon feed stream. A second portion of the coked catalyst is blended with the regenerated catalyst and introduced as blended catalyst to the reactor conduit.

In another embodiment, the first component of catalyst comprises a large pore molecular sieve and/or an amorphous material.

In further embodiments, the partial pressure of the hydrocarbons in the riser may be less than or equal to 172 kPa (25 psia); a diluent in the riser may be greater than or equal to 10 wt-% of the feed stream; the ratio of catalyst to feed in the riser may be greater than or equal to 10; and the ratio of coked catalyst to regenerated catalyst in the riser may be in the range of 0.3 to 3.0.

Another embodiment of the present invention is a process for fluidized catalytic cracking of a hydrocarbon feed stream to obtain light olefins. The process comprises contacting the hydrocarbon feed stream with a catalyst composition including at least 1.0 wt-% of the zeolite having no greater than medium average pore size and at least 0.1 wt-% coke. The contacting occurs in a single reactor for no more than 2 seconds.

In a further embodiment, the hydrocarbon partial pressure may be less than 172 kPa (25 psia) and the catalyst composition may be at a temperature of about 621° to 677° C. (1150° to 1250° F.) before contacting the feed stream.

Additional objects, embodiments, and details of this invention will become apparent from the following detailed description.

DETAILED DESCRIPTION OF THE INVENTION

Figure 1:
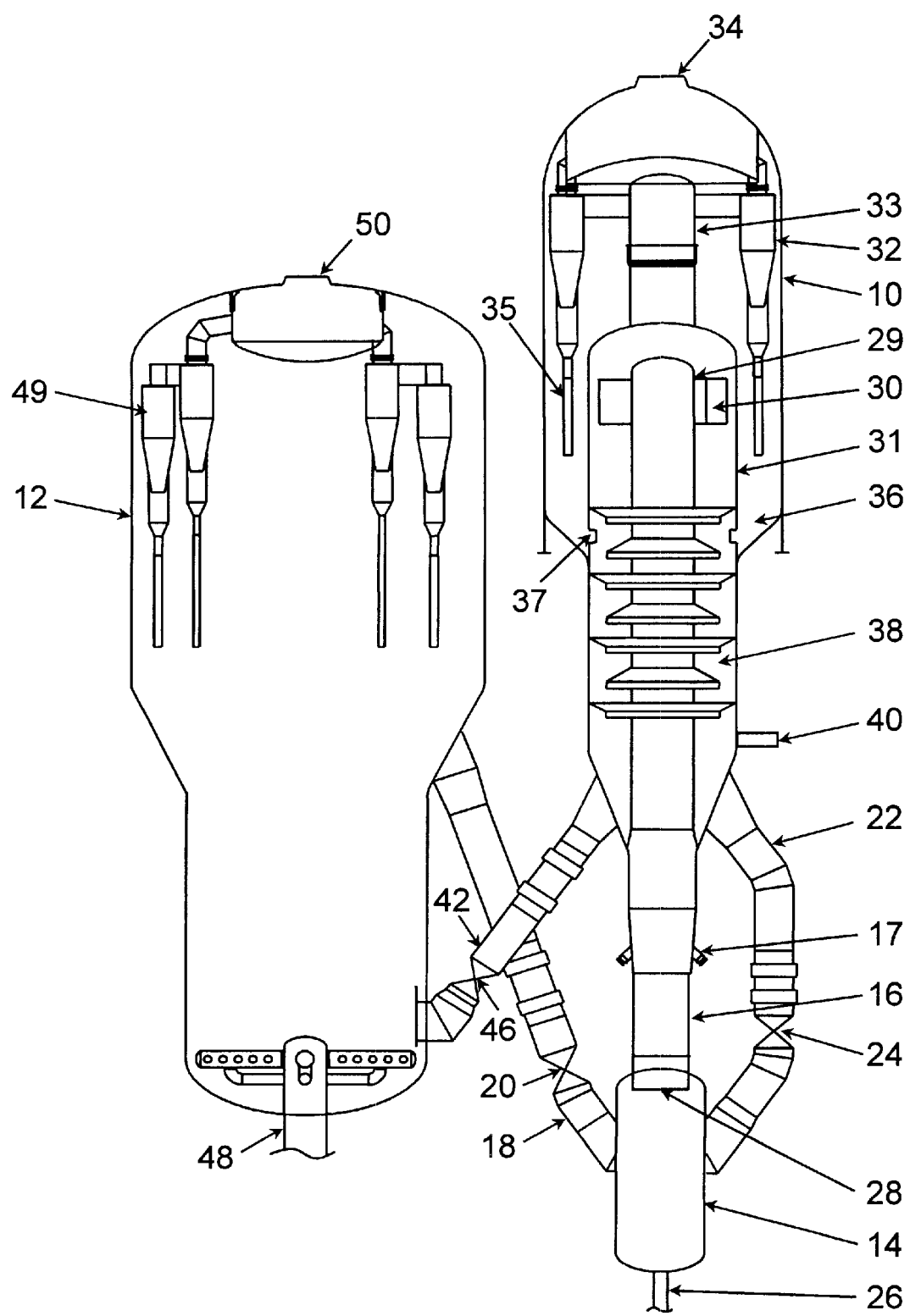
FIG. 1 is a schematic elevational view showing a FCC unit in accordance with the present invention.

This invention is more fully explained in the context of a FCC process that is modified to yield greater quantities of light olefins. Light olefins are olefin with six or less carbon atoms and, preferably, less than five carbon atoms. FIG. 1 shows a typical schematic arrangement of a FCC unit arranged in accordance with the present invention. The description of this invention in the context of the specific process arrangement shown is not meant to limit it to the details disclosed therein.

The FCC arrangement shown in FIG. 1 consists of a separator vessel 10, a regenerator 12, a blending vessel 14, and a vertical riser 16 that provides a pneumatic conveyance zone in which conversion takes place. The arrangement circulates catalyst and contacts feed in the manner hereinafter described.

The catalyst comprises two components that may or may not be on the same matrix. The two components are circulated throughout the entire system. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as an Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. We have found that Y zeolites with low rare earth content are preferred in the first catalyst component. Low rare earth content denotes less than or equal to about 1.0 wt-% rare earth oxide on the zeolite portion of the catalyst. Octacat™ catalyst made by W. R. Grace & Co. is a suitable low rare earth Y-zeolite catalyst.

The second catalyst component comprises a catalyst containing, medium or smaller pore zeolite catalyst exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium or smaller pore zeolites include ferrierite, erionite, and ST-5, developed by Petroleos de Venezuela, S.A. The second catalyst component preferably disperses the medium or smaller pore zeolite on a matrix comprising a binder material such as silica or alumina and an inert filer material such as kaolin. The second component may also comprise some other active material such as Beta zeolite. These catalyst compositions have a crystalline zeolite content of 10–25 wt-% or more and a matrix material content of 75–90 wt-%. Catalysts containing 25 wt-% crystalline zeolite material are preferred. Catalysts with greater crystalline zeolite content may be used, provided they have satisfactory attrition resistance. Medium and smaller pore zeolites are characterized by having an effective pore opening diameter of less than or equal to 0.7 nm, rings of 10 or fewer members and a Pore Size Index of less than 31.

The total catalyst composition should contain 1–10 wt-% of a medium to small pore zeolite with greater than or equal to 1.75 wt-% being preferred. When the second catalyst component contains 25 wt-% crystalline zeolite, the composition contains 4–40 wt-% of the second catalyst component with a preferred content of greater than or equal to 7 wt-%. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit.

The high concentration of the medium or smaller pore zeolite in the second component of the catalyst composition improve selectivity to light olefins by further cracking the lighter naphtha range molecules. But at the same time, the resulting smaller concentration of the first catalyst component still exhibits sufficient activity to maintain conversion of the heavier feed molecules to a reasonably high level.

FCC feedstocks, suitable for processing by the method of this invention, include conventional FCC feeds and higher boiling or residual feeds. The most common of the conventional feeds is a vacuum gas oil which is typically a hydrocarbon material having a boiling range of from 343° to 552° C. (650° to 1025° F.) and is prepared by vacuum fractionation of atmospheric residue. Heavy or residual feeds, i.e., boiling above 499° C. (930° F.), are also suitable. The FCC process of the present invention is suited best for feed stocks that are heavier than naptha range hydrocarbons boiling above about 177° C. (350° F.).

Looking then at FIG. 1, riser 16 provides a conversion zone for cracking of the feed hydrocarbons. Vertical riser 16 may have a smaller diameter than blending vessel 14, so that catalyst accelerates as it passes out of blending vessel 14 into riser 16. An embodiment of the present invention is that the residence time for the feed in contact with the catalyst in the riser is less than or equal to 2 seconds. Any residence time of less than or equal to 2 seconds may be preferred depending on the desired product distribution. The shorter residence time assures that the desired products once obtained do not convert to undesirable products. Hence, the diameter and height of the riser may be varied to obtain the desired residence time.

The riser typically operates with dilute phase conditions above the point of feed injection wherein the density is usually less than 320 kg/m$^3$ (20 lb/ft$^3$) and, more typically, less than 160 kg/m$^3$ (10 lb/ft$^3$). Feed is introduced into the riser by nozzle 17 between an inlet 28 to the riser and substantially upstream from an outlet 30. Volumetric expansion resulting from the rapid vaporization of the feed as it enters the riser further decreases the density of the catalyst within the riser to typically less than 160 kg/m$^3$ (10 lb/ft$^3$). Before contacting the catalyst, the feed will ordinarily have a temperature in a range of from 149° to 316° C. (300° to 600° F.). Additional amounts of feed may be added downstream of the initial feed point.

The blended catalyst and reacted feed vapors are then discharged from the top of riser 16 through an outlet 30 and separated into a cracked product vapor stream including olefins and a collection of catalyst particles covered with substantial quantities of coke and generally referred to as "coked catalyst." In an effort to minimize the contact time of the feed and the catalyst which may promote further conversion of desired products to undesirable other products, this invention can use any arrangement of separators to remove coked catalyst from the product stream quickly. In particular, a swirl arm arrangement 29, provided at the end of riser 16 can further enhance initial catalyst and cracked hydrocarbon separation by imparting a tangential velocity to the exiting catalyst and cracked product vapor stream mixture. Such swirl arm arrangements are more fully described in U.S. Pat. No. 4,397,738. The swirl arm arrangement is located in an upper portion of a chamber 31, and a stripping zone 38 is situated in the lower portion of the chamber 31. Catalyst separated by the swirl arm arrangement 29 drops down into the stripping zone 38. The cracked product vapor stream comprising cracked hydrocarbons including light olefin and some catalyst exit the chamber 31 via conduit 33 in communication with cyclones 32. The cyclones 32 remove remaining catalyst particles from the product vapor stream to reduce particle concentrations to very low levels. The product vapor stream then exits the top of separating vessel 10 through outlet 34. Catalyst separated by cyclones 32 return to separating vessel 10 through dipleg conduits 35 into dense bed 36 where it will enter the stripping zone through openings 37.

The stripping zone 38 removes adsorbed hydrocarbons from the surface of the catalyst by counter-current contact with steam. Steam enters stripping zone 38 through line 40.

The present invention recycles a first portion of the coked catalyst to the riser 16 without first undergoing regeneration. A second portion of the coked catalyst is regenerated in the regenerator 12 before it is delivered to the riser 16. The first and second portions of the catalyst may be blended in a blending vessel 14 before introduction to the riser 16. The recycled catalyst portion may be withdrawn from the stripping zone 38 for transfer to the blending vessel 14. The recycle conduit 22 transfers the first portion of the coked catalyst stripped of hydrocarbon vapors exiting stripping zone 38 back to blending vessel 14 as the recycled catalyst portion at a rate regulated by control valve 24. The second portion of the coked, stripped catalyst is transported to the regeneration zone through coked catalyst conduit 42 at a rate regulated by control valve 46 for the removal of coke.

On the regeneration side of the process, coked catalyst transferred to regenerator 12 via conduit 42 undergoes the typical combustion of coke from the surface of the catalyst particles by contact with an oxygen-containing gas. The oxygen-containing gas enters the bottom of regenerator 12 via an inlet 48 and passes through a dense fluidizing bed of catalyst (not shown). Flue gas consisting primarily of $CO_2$ and perhaps containing CO passes upwardly from the dense bed into a dilute phase of regenerator 12. A separator, such as cyclones 49 or other means, remove entrained catalyst particles from the rising flue gas before the flue gas exits the vessel through an outlet 50. Combustion of coke from the catalyst particles raises the temperatures of the catalyst which is withdrawn by regenerator standpipe 18.

Regenerator standpipe 18 passes regenerated catalyst from regenerator 12 into a blending vessel 14 at a rate regulated by control valve 20 where it is blended with recycled catalyst from separating vessel 10 via recycle conduit 22. Fluidizing gas passed into blending vessel 14 by conduit 26 contacts the catalyst and maintains the catalyst in a fluidized state to blend the recycled and regenerated catalyst.

The regenerated catalyst which is relatively hot is cooled by the unregenerated, coked catalyst which is relatively cool to reduce the temperature of the regenerated catalyst by 28° to 83° C. (50° to 150° F.) depending upon the regenerator temperature and the coked catalyst recycle rate. We have found that reducing the catalyst-to-feed contact results in an increased light olefin yield and a decreased dry gas yield. Other processes currently used in FCC operations to increase conversion result in poorer coke and dry gas selectivity.

The amount of blended catalyst that contacts the feed will vary depending on the temperature of the regenerated catalyst and the ratio of recycled to regenerated catalyst comprising the catalyst blend. The term "blended catalyst" refers to the total amount of solids that contact the feed and include both the regenerated catalyst from regenerator 12 and the recycled catalyst portion from the reactor side of the process. Generally, the blended catalyst to feed will be in a ratio of from 10 to 50. Preferably, the blended catalyst to feed will be in a ratio of from 10 to 30 and more preferably in a ratio of from 15 to 25. The high catalyst-to-feed ratio will operate to maximize conversion which tends to favor light olefin production.

Although it has been well established within the art of FCC that increasing catalyst-to-feed ratios will increase conversion, catalyst-to-feed ratios cannot be easily increased since this ratio is not an independent variable in standard FCC units. Rather the ratio of catalyst to feed is dependent on the heat balance limitations of the unit. Consequently, only relatively low catalyst-to-feed ratios of 4–10 are typically observed. One means of increasing the catalyst-to-feed ratio within the riser is to recycle coked catalyst along with regenerated catalyst back to the riser, because this avoids the heat balance limitations. Such a means of increasing catalyst-to-feed ratios, however, was not expected to maintain high catalyst activities due to the coke deactivation of the catalyst. Our research has revealed that blends of coked and regenerated catalyst have comparable activity to that of the regenerated catalyst. Consequently, recycling coked catalyst can be effectively utilized to increase the catalyst-to-feed ratios in the riser, thereby, allowing operation at very short catalyst-to-feed contact times with catalyst that has been heavily diluted with catalyst containing medium to small pore zeolite while still maintaining high conversions. Maximizing conversion is particularly important in order to maximize yields of key light olefins. Our discovery that the catalyst composition with a relatively low concentration of the first catalyst component and a relatively high concentration of the second catalyst component still exhibits improved conversion and selectivity to light olefin even when a portion of the catalyst composition is coked and when the riser residence time is very short was completely unexpected.

Ordinarily, the ratio of recycled catalyst to regenerated catalyst entering the blending zone will be in a broad range of from 0.1 to 5.0 and more typically in a range of from 0.3 to 3.0. Preferably, the blended catalyst will comprise a 1:1 ratio of recycled catalyst to regenerated catalyst. The amount of coke on the recycled catalyst portion returning to the blending vessel 14 will vary depending on the number of times the catalyst particle has recycled through the riser. Since the separation of the catalyst particles out of the riser is random, the coke content of the particles leaving the riser will be normally distributed, varying between the coke content of a particle going through the riser only once and the coke content of a particle that has gone through the riser many times. Nevertheless, the coked catalyst portion entering the regeneration zone as well as the recycled catalyst portion could range from an average coke concentration of between 0.3 to 1.1 wt-%. The preferred range of average coke concentration is 0.5 to 1.0 wt-%. Moreover, the blended catalyst composition will contain at least 0.1 wt-% coke before contacting the feed.

When the blending vessel 14 is used, blending of catalyst portions should occur for sufficient time to achieve substantially thermal equilibrium. Further details regarding conditions in the blending vessel are given in U.S. Pat. No. 5,597,537.

Regenerated catalyst from regenerator standpipe 18 will usually have a temperature in a range from 677° to 760° C. (1250° to 1400° F.) and, more typically, in a range of from 699° to 760° C. (1290° to 1400° F.). The temperature of the recycled catalyst portion will usually be in a range of from 510° to 621° C. (950° to 1150° F.). The relative proportions of the recycled and regenerated catalyst will determine the temperature of the blended catalyst mixture that enters the riser. The blended catalyst mixture will usually range from about 593° to 704° C. (1100° to 1300° F.) and, more preferably at about 649° C. (1200° F.).

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10–55 wt-% of feed and preferably about 15 wt-% of feed. Other diluents such as dry gas can be used to reach equivalent hydrocarbon partial pressures.

The temperature of the cracked stream at the riser outlet will be about 510° to 621° C. (950° to 1150° F.). However, we have found that riser outlet temperatures above 566° C. (1050° F.) make more dry gas and little more olefins. Whereas, riser outlet temperatures below 566° C. (1050° F.) make less ethylene and propylene. Thus, a temperature around 1050° F. appears to be optimal.

EXAMPLE 1

We conducted a study to determine the benefits of reducing riser contact time effects in the presence of a catalyst composition containing a large quantity of a small to medium pore zeolite component, and in a process system where the temperature of the catalyst contacting the feed is representative of a recycled catalyst system. The study was conducted in a FCC riser operating under conditions favorable to obtain greater yields of light olefin. Tests were performed using three riser residence times: 2.5 seconds, 1.5 seconds, and 0.7 seconds. A riser in the FCC process was run at 141 kPa (20.5 psia), a regenerator temperature of around 654° C. (1210° F.), an outlet temperature of 566° C. (1050° F.), a feed temperature of about 121° C. (250° F.), a riser hydrocarbon partial pressure of about 76 kPa (11 psia), and a catalyst-to-feed ratio of about 28. The feed was High Sulfur Diesel and the catalyst composition was a mixture of 80 wt-% Octacat™, a Y-type zeolite catalyst component and 20 wt-% of an additive containing about 25 wt-% ST-5 medium pore zeolite. The conversion reported in this study, 37° C., was chosen to highlight conversion towards lighter hydrocarbons rather than the standard FCC conversion, 221° C., which highlights conversion to naphtha. The results for each of the residence times in the riser are presented in Table I.

TABLE I

| | Riser Time (sec.) | | |
|---|---|---|---|
| | 0.7 | 1.5 | 2.5 |
| Dry Gas $H_2$—$C_2$ (wt-%) | 2.29 | 2.78 | 4.11 |
| Ethylene (wt-%) | 5.96 | 6.88 | 6.02 |
| Propylene (wt-%) | 21.64 | 22.30 | 19.36 |
| Butylene (wt-%) | 14.12 | 13.41 | 12.56 |
| Conversion at 37° C. (wt-%) | 60.4 | 62.4 | 58.1 |

Decreasing the residence time in the riser from 2.5 seconds to 0.7 seconds increased the relative propylene yield by 12% with a corresponding decrease in dry gas of 44%. This corresponds to an absolute yield increase of 2.3 wt-% propylene and 1.8 wt-% decrease in dry gas. Decreasing the residence time in the riser from 2.5 seconds to 1.5 seconds increased the relative propylene yield by 15% with the corresponding decrease in dry gas of 32%. Ethylene production increased in 1.5 second riser residence time and nominally decreased at 0.7 second riser residence time. Additionally, butylene production increased with reductions in riser residence time.

Surprisingly, the 2.5 second residence time actually experienced lower conversion than the shorter times of 1.5 or 0.7 seconds. We attribute this drop in conversion due to a reduction of secondary reactions such as olefin oligomerization, which produce higher molecular weight components. Consequently, some of the yield advantages at lower riser times are due to a preservation of olefins in the riser, which not only increases olefin yields but maintains conversion by preventing the reformation of material boiling higher than 37° C. We believe the conversion drop that was observed when the riser time was lowered from 1.5 to 0.7 seconds was due to insufficient cracking time although the conversion was still higher than that obtained at 2.5 seconds due to a reduction in secondary reactions that form heavier molecules.

EXAMPLE 2

One of the benefits of the present invention is that recycling of coked catalyst and mixing it with regenerated catalyst can reduce the catalyst temperature entering the riser by 28° to 83° C. (50° to 150° F.), depending on the regenerator temperature and the coked catalyst recycle rate. A study was conducted to demonstrate the effect of lower catalyst temperature contacting the feed in a short riser residence time system where the catalyst contained a high concentration of a medium pore zeolite. The effect of catalyst temperature contacting the feed was observed at 649° C. (1200° F.) and 732° C. (1350° F.) with catalyst composition containing 20 wt-% of an additive containing about 25 wt-% ST-5 medium pore zeolite and 80 wt-% of Octacat™, a catalyst containing Y-type zeolite. Tests were performed at 141 kPa (20.5 psia) with a hydrocarbon partial pressure of 76 kPa (11 psia), 566° C. (1050° F.) riser outlet temperature, 149° C. (300° F.) feed temperature, and a riser contact time of 1.5 seconds. The feed used was a blend of 78 wt-% straight run diesel and 12 wt-% atmospheric gas oil. The high catalyst temperature, 732° C. (1350° F.), was chosen to represent a standard FCC regenerator temperature. The lower catalyst inlet temperature of 649° C. (1200° F.) resulted in a catalyst-to-feed ratio of 28 compared to the catalyst-to-feed ratio of 12 used for the hotter catalyst inlet temperature of 732° C. (1350° F.). Since the riser outlet temperature was maintained at 566° C. (1050° F.) in both cases, decreasing the catalyst inlet temperature forces operation at higher catalyst-to-feed ratio in the riser. Inert catalysts in an amount of 60 wt-% was blended with the Octacat™ catalyst in an amount of 40 wt-% for the cooler catalyst temperature in order to reduce the catalyst activity and achieve a conversion that is comparable to the conversion obtained with the higher catalyst temperature. Again, the conversion reported in this study, 37° C., was chosen to highlight conversion towards lighter hydrocarbons rather than the standard FCC conversion, 221° C., which highlights conversion to naphtha. The results are presented in Table II.

TABLE II

| | Catalyst Temperature | |
|---|---|---|
| | 732° C. (1350° F.) | 649° C. (1200° F.) |
| Catalyst-to-Feed Ratio | 12 | 28 |
| Inert Catalyst (wt-%) | 0 | 60 |
| Dry Gas (wt-%) | 4.07 | 2.97 |
| Ethylene (wt-%) | 5.31 | 5.31 |
| Propylene (wt-%) | 16.97 | 20.69 |
| Butylene (wt-%) | 12.67 | 14.52 |
| Gasoline (wt-%) | 26.32 | 22.98 |
| Conversion at 37° C. (wt-%) | 54.6 | 55.6 |

The comparison of the effect of catalyst temperature on propylene yield indicates that reducing the catalyst inlet temperature by 66° C. (150° F.) results in a 22% relative increase and a 3.7 wt-% absolute increase in propylene yield. Additionally, a 15% relative increase and a 1.9 wt-% absolute increase in butylenes and a 27% relative decrease and a 1.1 wt-% absolute decrease in dry gas was observed with the reduction in catalyst inlet temperature. Conversion for the lower catalyst temperature was also improved.

EXAMPLE 3

We compared the performance of a fully regenerated catalyst and a blend containing 50 wt-% coked catalyst and 50 wt-% regenerated catalyst. The tests were performed in a circulating riser pilot plant, which has the capability of recycling coked catalyst and regenerated catalyst to the riser. The amount of coke on the regenerated catalyst was about 0.01 wt-%, whereas, the amount of coke on the 50/50 coked/regenerated blend was between 0.27 and 0.35 wt-%. The feed used in the study was a West Texas Intermediate Vacuum Gas Oil with a boiling point range of 274° to 573° C. (526° to 1063° F.). The catalyst used was a typical Y-type zeolite containing FCC catalyst called Orion™ produced by W. R. Grace & Co., which was previously used in a commercial FCC unit to insure that equilibrium activity was reached. The key riser pilot plant tests were all performed with a riser outlet temperature of 515° C. (960° F) and a riser pressure of 241.3 kPa (35 psia).

Figure 2:
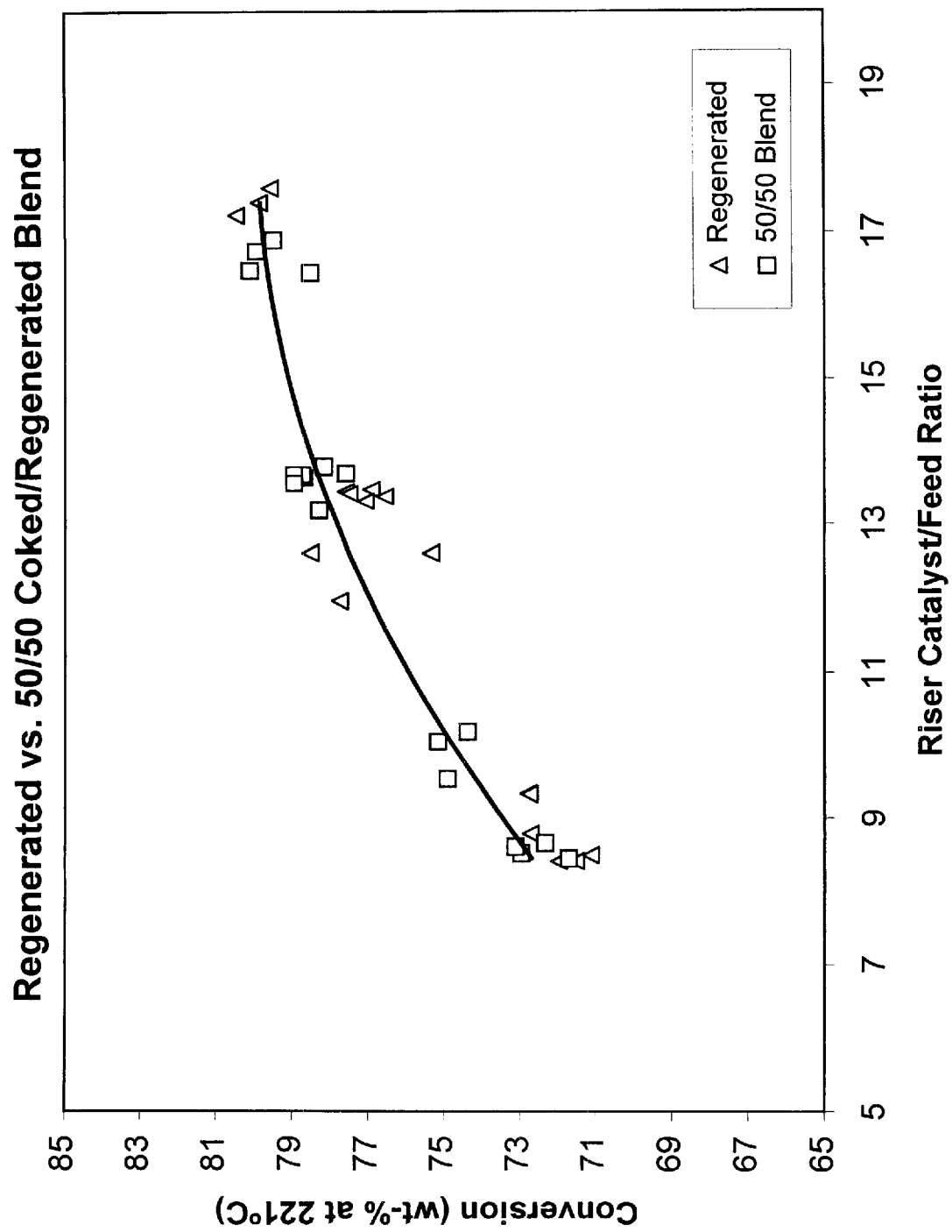
FIG. 2 is a graph comparing conversion for regenerated and blended catalyst compositions.

Surprisingly, the results of these tests illustrated in FIG. 2 reveal that the fully regenerated catalyst and the blend containing 50 wt-% recycled, coked catalyst and 50% fully regenerated catalyst have comparable activities. Over a wide range of catalyst-to-oil ratios tested in the riser, similar conversion of the feed to gasoline or light material (221° C. (430° F.)) was observed. The catalyst evaluated in these tests did not contain any small to medium pore zeolite. These smaller pore zeolites have high resistivity to coke. We, therefore, expect them to maintain activity when recycled without regeneration.

EXAMPLE 4

We conducted another study to compare feed conversion over varying concentrations of a component additive containing ZSM-5. These tests were performed in a riser pilot plant using a Diesel/Atmospheric Gas Oil blend (78%/22%) with a boiling point range of 239° to 472° C. (463° to 882° F). The catalyst composition included Octacat™, Y-type zeolite, standard FCC catalyst taken from a commercial FCC unit to insure equilibrated activity and Olefins Max™, an additive manufactured by W.R. Grace & Co., which contained 25 wt-% of ZSM-5. The additive level was varied from 0 to 40%. All tests were run with a catalyst to feed ratio of about 28, a riser outlet temperature of 566° C. (1050° F), a riser partial pressure was 79.3 kPa (11.5 psia), and a feed-to-catalyst contact time in the riser of 1.5 seconds.

Interestingly, we discovered that increasing the additive to very high levels had only a marginal affect on the conversion to light materials that boil under 37° C. (98° F.). The data is illustrated in Table III. Although the conversion does drop slightly from 61.9 to 60.0 wt-% as the additive level is increased from 10 to 40 wt-%, the data indicates that the activity of the standard, Y-type zeolite, FCC catalyst has been well maintained even after high dilution. Since the ZSM-5 additive can only crack lighter, naptha-range molecules, ZSM-5 addition had been thought to significantly reduce feed conversion at higher levels. Our tests show that significant feed conversion can be achieved at very high medium pore zeolite additive levels and short catalyst-tofeed contact time using higher than typical catalyst-to-feed ratios.

TABLE III

| Additive Level. (wt-%) | 0 | 10 | 20 | 30 | 40 |
|---|---|---|---|---|---|
| Conversion to 98 F. (wt-%) | 59.2 | 61.9 | 61.3 | 60.8 | 60.0 |
| Coke (wt-%) | 3.51 | 2.78 | 2.46 | 2.30 | 1.88 |
| Dry Gas (wt-%) | 3.36 | 3.16 | 3.18 | 2.71 | 2.83 |
| Ethylene (wt-%) | 2.80 | 5.01 | 5.61 | 6.15 | 7.51 |
| Propylene (wt-%) | 16.21 | 20.32 | 20.78 | 21.33 | 21.73 |
| Butylene (wt-%) | 14.55 | 14.43 | 14.18 | 13.67 | 12.97 |

What is claimed is:

1. A process for fluidized catalytic cracking of a hydrocarbon feed stream to obtain light olefins, said process comprising:

contacting the hydrocarbon feed stream with a blended catalyst comprising regenerated catalyst and coked catalyst, said catalyst having a catalyst composition including a first component comprising a large pore molecular sieve and a second component comprising a zeolite with no greater than medium pore size, said zeolite with no greater than medium pore size comprising at least 1.0 wt-% of the catalyst composition, said contacting occurring in a riser to crack hydrocarbons in said feed stream and obtain a cracked stream containing hydrocarbon products including light olefins and coked catalyst;

passing said cracked stream out of an end of said riser such that said hydrocarbon feed stream is in contact with the blended catalyst in the riser for less than or equal to 2 seconds on average;

separating said hydrocarbon products including light olefins from said coked catalyst;

passing a first portion of said coked catalyst to a regeneration zone and combusting coke from said catalyst to produce regenerated catalyst, said regenerated catalyst having substantially the same relative proportions of the first component and the second component as the blended catalyst that contacts the hydrocarbon feed stream;

blending a second portion of said coked catalyst with said regenerated catalyst to make the blended catalyst; and introducing said blended catalyst to said riser.

2. The process of claim 1 wherein said first catalyst component comprises no more than 80 wt-% of the catalyst composition.

3. The process of claim 1 wherein said molecular sieve is selected from a group consisting of an X zeolite and a Y zeolite.

4. The process of claim 1 wherein said second portion of said coked catalyst and said regenerated catalyst are blended outside of the riser before contacting said feed stream.

5. The process of claim 1 wherein a partial pressure of said hydrocarbons in said riser is less than or equal to 172 kPa (25 psia).

6. The process of claim 1 wherein an amount of diluent in said riser is greater than or equal to 10 wt-% of the feed stream.

7. The process of claim 1 wherein a weight ratio of the blended catalyst to the feed stream in the riser is greater than or equal to 10.

8. The process of claim 1 wherein a weight ratio of the coked catalyst to the regenerated catalyst in the riser is in a range of 0.3 to 3.0.

9. The process of claim 1 wherein the temperature of the cracked stream at the top end of the riser is in the range of 510° to 621° C. (950° to 1150° F.).

10. The process of claim 1 wherein the temperature of the blended catalyst is greater than or equal to 28° C. (50° F.) lower than a temperature of the regenerated catalyst coming from the regeneration zone.

11. The process of claim 1 wherein said zeolite with no greater than medium pore size comprises at least 1.75 wt-% of the blended catalyst composition.

12. A process for fluidized catalytic cracking of a hydrocarbon feed stream to obtain light olefins, said process comprising:

contacting the hydrocarbon feed stream with a blended catalyst at an initial temperature of 621° to 677° C. (1150° to 1250° F.) in a riser to crack hydrocarbons in said feed stream and obtain a cracked stream containing hydrocarbon products including light olefins and coked catalyst, said blended catalyst comprising regenerated catalyst and coked catalyst, said catalyst having a catalyst composition including a first component comprising a large pore zeolite and/or an active amorphous material and a second component comprising a molecular sieve with no greater than medium average pore size;

passing said cracked stream out of said riser at a temperature of 538° to 593 ° C. (1000° to 1100° F.) such that said hydrocarbon feed stream is in contact with the blended catalyst in the riser for less than 2 seconds on average;

separating said hydrocarbon products including light olefins from said coked catalyst;

passing a first portion of said coked catalyst to a regeneration zone and combusting coke from said catalyst to produce regenerated catalyst, said regenerated catalyst having substantially the same relative proportions of the first catalyst component and the second catalyst component as the blended catalyst that contacts the hydrocarbon feed stream;

blending a second portion of said coked catalyst with said regenerated catalyst; and introducing said blended catalyst to said reactor conduit.

13. The process of claim 12 wherein said first component of catalyst includes a material selected from one of a large pore molecular sieve and an amorphous material.

14. The process of claim 12 wherein said partial pressure of said hydrocarbons in said riser is less than or equal to 172 kPa (25 psia).

15. The process of claim 12 wherein a diluent in said riser is greater than or equal to 10 wt-% of the feed stream.

16. The process of claim 12 wherein the ratio of catalyst to feed in the riser is greater than or equal to 10.

17. The process of claim 12 wherein the ratio of the coked catalyst to the regenerated catalyst in the riser is in the range of 0.3 to 3.0.

* * * * *